(12) United States Patent
Tramontina (10) Patent No.: US 7,731,056 B2
(45) Date of Patent: Jun. 8, 2010

(54) DISPENSER ASSEMBLY FOR DISPENSING GLOVES INCLUDING A CARTRIDGE AND A DISPENSER WITH A GLOVE PUSHER

(75) Inventor: Paul Francis Tramontina, Alpharetta, GA (US)

(73) Assignee: Kimberly-Clark Worldwide, Inc., Neenah, WI (US)

(*) Notice: Subject to any disclaimer, the term of this patent is extended or adjusted under 35 U.S.C. 154(b) by 774 days.

(21) Appl. No.: 11/469,030

(22) Filed: Aug. 31, 2006

(65) Prior Publication Data
US 2007/0215635 A1    Sep. 20, 2007

Related U.S. Application Data

(60) Provisional application No. 60/743,575, filed on Mar. 20, 2006.

(51) Int. Cl.
B65H 3/00 (2006.01)
(52) U.S. Cl. .............................. 221/36; 221/37; 221/40; 221/41; 221/50; 221/254
(58) Field of Classification Search ................ 221/259, 221/254, 36, 37, 40, 41, 46, 49, 50
See application file for complete search history.

(56) References Cited

U.S. PATENT DOCUMENTS

| | | |
|---|---|---|
| 1,959,614 A | 5/1934 | Coons |
| 2,122,637 A | 7/1938 | Colburn |
| 2,591,855 A | 4/1952 | Nicholson |
| 2,795,353 A | 6/1957 | Tuttle |
| 3,174,643 A | 3/1965 | Carlson |
| 3,343,716 A | 9/1967 | Peebles |
| 3,517,855 A * | 6/1970 | Hillis .......................... 221/259 |
| 4,623,074 A * | 11/1986 | Dearwester ................... 221/48 |
| 4,773,532 A | 9/1988 | Stephenson |
| 4,844,293 A | 7/1989 | McLaughlin |

(Continued)

FOREIGN PATENT DOCUMENTS

DE      8715996 U1    2/1988

(Continued)

*Primary Examiner*—Gene Crawford
*Assistant Examiner*—Timothy R Waggoner
(74) *Attorney, Agent, or Firm*—Sue C. Watson; Douglas L. Miller; Ralph H. Dean, Jr.

(57) ABSTRACT

A dispenser for dispensing gloves is provided which includes a housing having an exit port, the housing also formed to include a compartment which is configured to hold a plurality of gloves therein. The dispenser includes a glove pusher movably coupled to the housing. At least a portion of the glove pusher is configured to move within the compartment of the housing and push at least a portion of a glove disposed in the compartment through the exit port. A cartridge configured to be disposed into a compartment of a dispenser is disclosed. The cartridge is formed to permit a portion of a dispenser to move into the internal compartment of the cartridge to move at least one of the plurality of gloves at least partially through the at least one opening in the cartridge. A dispensing assembly also may include a stack of gloves or a cartridge containing a plurality of gloves. A method of using a glove dispenser is also provided.

15 Claims, 5 Drawing Sheets

U.S. PATENT DOCUMENTS

| | | | |
|---|---|---|---|
| 4,909,413 A | 3/1990 | McCutcheon | |
| 4,941,591 A * | 7/1990 | Lin et al. | 221/100 |
| 4,953,747 A | 9/1990 | Wenkman et al. | |
| 4,993,589 A | 2/1991 | McLaughlin | |
| 4,997,105 A | 3/1991 | Fischer | |
| 5,024,349 A | 6/1991 | Haenni et al. | |
| 5,096,089 A | 3/1992 | McLaughlin | |
| 5,570,808 A | 11/1996 | Tassoni | |
| 5,816,440 A | 10/1998 | Shields et al. | |
| 5,921,434 A | 7/1999 | Hollander et al. | |
| 5,992,683 A | 11/1999 | Sigl | |
| 5,997,928 A | 12/1999 | Kaish et al. | |
| 6,021,919 A | 2/2000 | Kelly | |
| 6,062,421 A * | 5/2000 | Marley | 221/45 |
| 6,422,416 B1 | 7/2002 | Tramontina | |
| 6,443,327 B1 | 9/2002 | Chen | |
| 6,708,841 B2 | 3/2004 | Baughman | |
| 6,832,697 B2 * | 12/2004 | Lai | 221/210 |
| 2002/0113079 A1 | 8/2002 | Corbett | |
| 2003/0201276 A1 | 10/2003 | Fuller | |
| 2003/0230591 A1 | 12/2003 | Jordan et al. | |
| 2004/0099623 A1 | 5/2004 | Kurtz et al. | |
| 2004/0182874 A1 | 9/2004 | Kringel et al. | |

FOREIGN PATENT DOCUMENTS

| | | |
|---|---|---|
| DE | 29818035 | 3/1989 |
| DE | 29616735 | 2/1997 |
| EP | 0305236 | 4/1999 |
| FR | 2776269 | 9/1999 |

\* cited by examiner

DISPENSER ASSEMBLY FOR DISPENSING GLOVES INCLUDING A CARTRIDGE AND A DISPENSER WITH A GLOVE PUSHER

CROSS-REFERENCE TO RELATED APPLICATIONS

This application claims priority to provisional U.S. Application Ser. No. 60/743,575, filed Mar. 20, 2006, entitled "Dispenser Assembly For Dispensing Gloves Including A Cartridge And A Dispenser With A Glove Pusher," by Paul Francis Tramontina.

BACKGROUND OF THE INVENTION

This invention relates to a dispenser adapted to dispense gloves and configured to hold a cartridge or container containing a plurality of gloves. Hospital, laboratory or industrial glove dispensing systems typically consist of quantities of gloves that are contained in a corrugated box with a perforated region. When the perforated region is removed, an opening is provided through which gloves are withdrawn by a user. Problems exist with this system.

The opening is sized such that gloves often partially protrude therethrough. The size of the opening may permit the gloves adjacent thereto and/or protruding therethrough to become contaminated. Alternatively, when the box becomes nearly empty, the opening permits unwanted particles, contaminates, and the like to enter the box. Conversely, when the box is full, it may be difficult for a user to withdrawn one glove at a time, because multiple gloves may block the opening. In this instance, when attempting to withdraw a single glove, additional gloves may inadvertently be withdrawn or fall out of the box, resulting in waste. When the box becomes nearly depleted, a user may need to put his/her hand into the box to withdraw one or more gloves. This action may introduce contamination into the box as well.

Accordingly, there is a need for a dispenser and/or a dispensing assembly which desirably includes a dispenser and may include a cartridge configured to holding a plurality of gloves. Such a dispenser assembly desirably permits a plurality of gloves to be easily dispensed one at a time. The dispenser desirably operates to present one glove at a time to a user, thereby minimizing the introduction of contaminants into the cartridge and plurality of gloves. In addition, waste due to inadvertent multiple dispensing of gloves is also greatly reduced. Further, the opening to the cartridge and/or dispenser is desirably configured and positioned to minimize the likelihood of contaminants entering the cartridge.

Such a dispenser assembly would be easily assembled and easily mounted, if desired, for use on a surface. Such a dispenser would desirably be made from a material which would provide some resistance to air borne, liquid and/or solid contaminants.

SUMMARY OF THE INVENTION

In response to the issues described herein, a dispenser for dispensing gloves is provided. The dispenser comprises a housing formed to include a compartment therein. The housing is configured to hold a plurality of gloves in the compartment. The housing also has an exit port. A glove pusher is movably coupled to the housing. At least a portion of the glove pusher is configured to move within the compartment of the housing and to push at least a portion of a glove disposed in the compartment through the exit port.

In another aspect of the invention, a cartridge adapted to hold a plurality of gloves configured to be positioned in a dispenser is provided. The dispenser is configured to be positioned in a dispenser that has a housing formed to include a compartment which is configured to hold a cartridge. The dispenser housing includes an exit port. The dispenser for the cartridge also includes a glove pusher movably coupled to the housing. At least a portion of the glove pusher is configured to move within the compartment of the housing to push at least a portion of a glove through the exit port. The cartridge comprises a plurality of walls which cooperate to form an inner surface and an internal compartment configured to hold a plurality of gloves. The cartridge has at least one opening. The cartridge also has a plurality of gloves provided in a stack disposed in the internal compartment. The cartridge is configured to be disposed into a compartment of a dispenser. The cartridge is formed to permit a portion of a dispenser to move into the internal compartment of the cartridge to move at least one of the plurality of gloves at least partially through the at least one opening in the cartridge.

In yet another aspect of the invention, a dispensing assembly adapted for dispensing gloves is provided. The dispensing assembly comprises a dispenser. The dispenser includes a housing formed to include a compartment therein. The housing is configured to hold a plurality of gloves in the compartment. The housing includes an exit port. The dispenser includes a glove pusher movably coupled to the housing. At least a portion of the glove pusher is configured to move within the compartment of the housing and to push at least a portion of a glove through the exit port. The dispensing assembly also includes a cartridge. The cartridge comprises a plurality of walls which cooperate to form an inner surface and an internal compartment configured to hold a plurality of gloves. The cartridge has at least one opening. The cartridge further includes a plurality of gloves provided in a stack disposed in the internal compartment. The cartridge is configured to be disposed into the compartment of the dispenser housing. The cartridge is formed to permit the glove pusher of the dispenser to move into the internal compartment of the cartridge to contact and move at least one of the plurality of gloves at least partially through the at least one opening in the cartridge and the exit port of the dispenser.

In a further aspect of the invention, a dispensing system adapted for dispensing gloves is provided. The dispensing system comprises a dispenser. The dispenser includes a housing formed to include a compartment therein. The housing is configured to hold a plurality of gloves in the compartment. The housing includes an exit port. The dispenser also includes a glove pusher movably coupled to the housing. At least a portion of the glove pusher is configured to move within the compartment of the housing. The dispensing system also includes a plurality of gloves provided in a stack disposed in the compartment. The glove pusher is positioned to contact and move at least a portion of one of the plurality of gloves in the stack at least partially through the exit port of the dispenser.

In still yet another aspect of the invention, a method for dispensing gloves is provided. The method includes providing a dispensing assembly. The dispensing assembly includes a dispenser and a cartridge. The dispenser is adapted for dispensing gloves. The dispenser includes a housing formed to include a compartment therein. The housing is configured to hold a plurality of gloves in the compartment. The housing includes an exit port. The dispenser also includes a glove pusher movably coupled to the housing. At least a portion of the glove pusher is configured to move within the compartment of the housing and to push at least a portion of a glove through the exit port. The method also includes providing a cartridge. The cartridge comprises a plurality of walls which cooperate to form an inner surface and an internal compartment configured to hold a plurality of gloves. The cartridge has at least one opening. A plurality of gloves are provided in a stack disposed in the internal compartment. The method also includes disposing the cartridge in the compartment of the housing such that at least one opening in the cartridge is positioned in alignment with the exit port of the housing. The method further includes positioning the glove pusher in the internal compartment of the cartridge such that the glove pusher contacts at least one glove in the compartment. Finally, the method includes moving the glove pusher such that the glove pusher moves a portion of at least a portion of one glove through at least one opening in the cartridge and the exit port of the housing of the dispenser.

DEFINITIONS

As used herein, the term "glove" or "plurality of gloves" refers to a covering for a user's hand, and desirably, but not by way of limitation, includes four fingers and a thumb, an area covering a palm and a back of a user's hand, as well as a cuff positioned generally around a user's wrist. Each glove may be constructed from one or more materials. Such materials may include, for example, but not by way of limitation, a woven material, a nonwoven material, a knitted material, and so forth. In addition, as a further example only, each glove may be constructed from one or more natural or synthetic materials such as latex, nitrile, and so forth.

As used herein, the terms "comprise", "comprises", "comprising" and other derivatives from the root term "comprise" are intended to be open-ended terms that specify the presence of any stated features, elements, integers, steps, or components, but do not preclude the presence or addition of one or more other features, elements, integers, steps, components, or groups thereof. Similarly, the terms "include". "includes", "has" and/or "have", and derivatives thereof, are intended to be interpreted as the word "comprise", and are intended to be open-ended terms that specify the presence of any stated features, elements, integers, steps, or components, but do not preclude the presence or addition of one or more other features, elements, integers, steps, components, or groups thereof.

As used herein, the terms "contaminate", "contaminant" and/or "contamination" mean to make unclean or impure by contact. Such contact may be by liquid, solid and/or gas. For example, but not by way of limitation, mud that befouls shoes; noxious fumes that foul the air; bodily fluids that foul clean diapers.

As used herein, the term "exit port" and/or "dispensing opening" refers to an opening in a dispenser or a cartridge, respectively, for the passage of one or more gloves therethrough.

As used herein, the term "fasteners" means devices that fasten, join, connect, secure, hold, or clamp components together. Fasteners include, but are not limited to, screws, nuts and bolts, rivets, snap-fits, tacks, nails, loop fasteners, and interlocking male/female connectors, such as fishhook connectors, a fish hook connector includes a male portion with a protrusion on its circumference. Inserting the male portion into the female portion substantially permanently locks the two portions together.

As used herein, the term "couple" includes, but is not limited to, joining, connecting, fastening, linking, or associating two things integrally or interstitially together.

As used herein, the term "configure" or "configuration" means to design, arrange, set up, or shape with a view to specific applications or uses. For example: a military vehicle that was configured for rough terrain; configured the computer by setting the system's parameters.

As used herein, the term "hinge" refers to a jointed or flexible device that connects and permits pivoting or turning of a part to a stationary component. Hinges include, but are not limited to, metal pivotable connectors, such as those used to fasten a door to frame, and living hinges. Living hinges may be constructed from plastic and formed integrally between two members. A living hinge permits pivotable movement of one member in relation to another connected member.

As used herein, the term "substantially" refers to something which is done to a great extent or degree; a significant or great amount; for example, as used herein "substantially" as applied to "substantially" covered means that a thing is at least 90% covered.

As used herein, the term "alignment" refers to the spatial property possessed by an arrangement or position of things in a straight line or in parallel lines.

As used herein, the terms "orientation" or "position" used interchangeably herein refer to the spatial property of a place where or way in which something is situated; for example, "the position of the hands on the clock."

As used herein, the term "about" refers to an amount that is plus or minus 10 percent of a stated or implied range.

These terms may be defined with additional language in the remaining portions of the specification.

DETAILED DESCRIPTION

Reference will now be made in detail to one or more embodiments of the invention, examples of which are illustrated in the drawings. Each example and embodiment is provided by way of explanation of the invention, and is not meant as a limitation of the invention. For example, features illustrated or described as part of one embodiment may be used with another embodiment to yield still a further embodiment. It is intended that the invention include these and other modifications and variations as coming within the scope and spirit of the invention.

Figure 1:
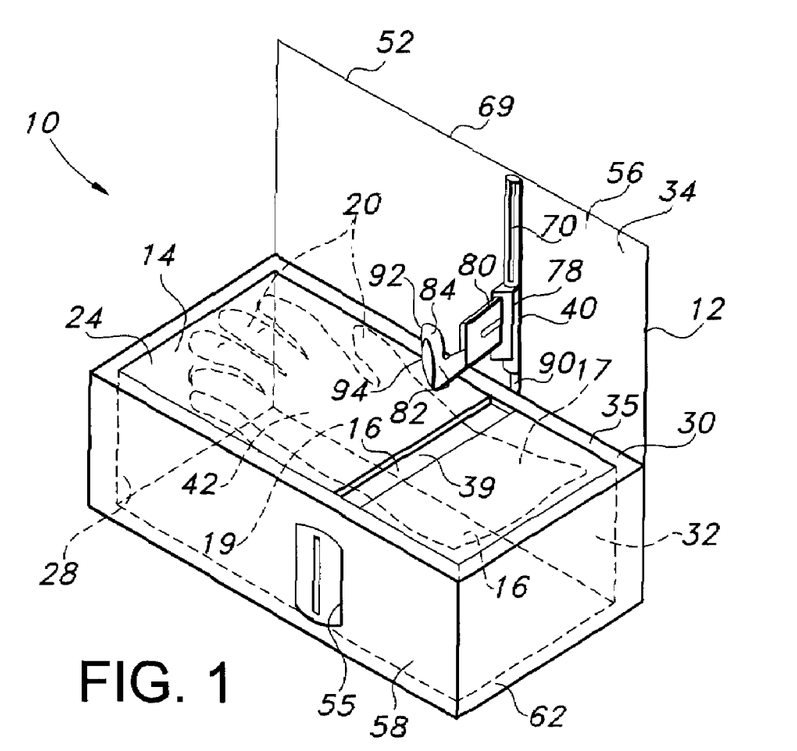
FIG. 1 is an upper perspective view of a dispensing assembly of the present invention showing a dispenser having a cartridge positioned therein, the cartridge including a plurality of gloves disposed therein (the cartridge and the plurality of gloves illustrated partially by phantom lines), and the dispenser including a glove pusher.
Figure 2:
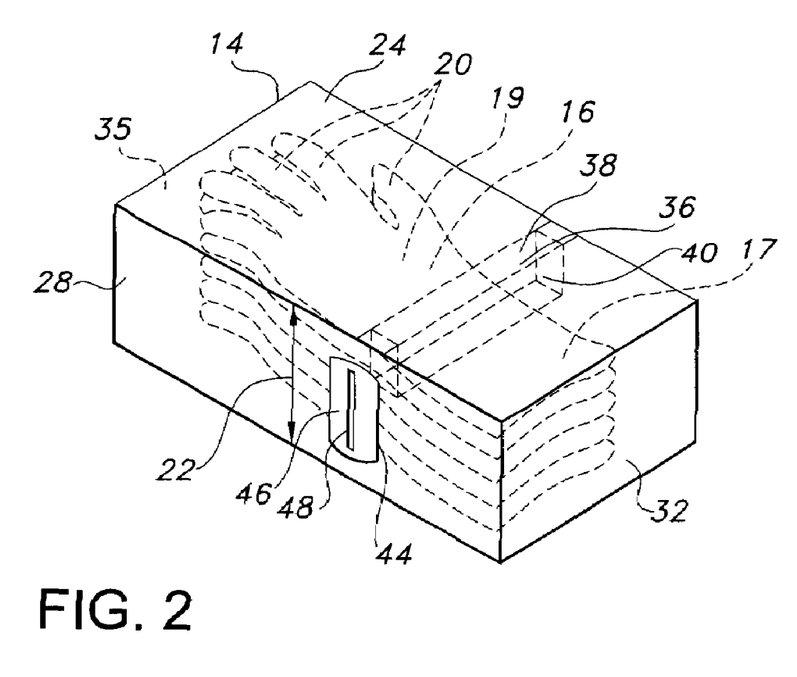
FIG. 2 is an upper perspective view of a cartridge similar to the cartridge of FIG. 1, but showing the plurality of gloves positioned therein and aligned wrist area to wrist area in a dispensing position and a removable glove holder, the gloves and the glove holder illustrated via phantom lines.
Figure 3:
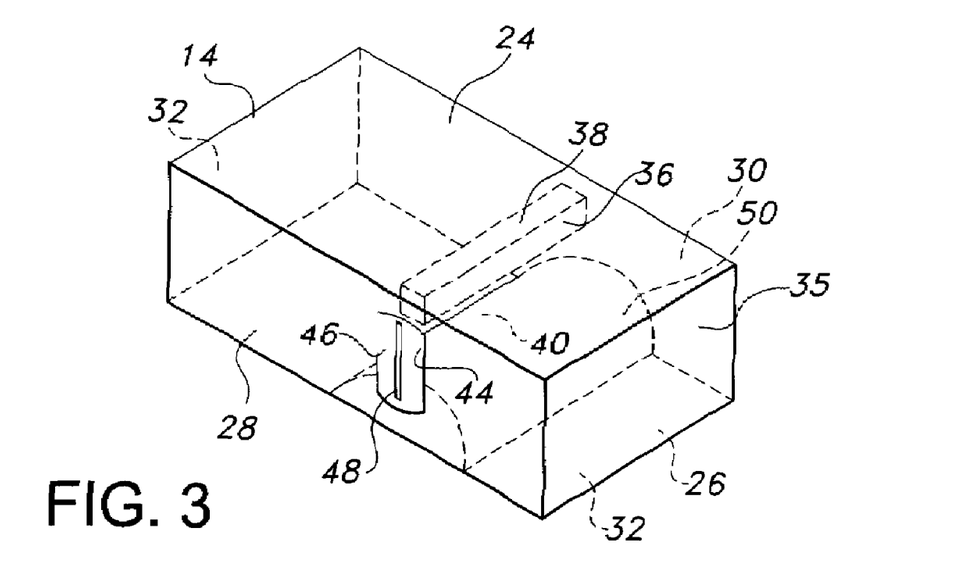
FIG. 3 is an upper perspective view of the cartridge of FIG. 2, but showing a curved section positioned on a lower wall of the cartridge and perforations on an upper wall which permit the removal of the glove holder, the gloves not visible in the view.
Figure 4:
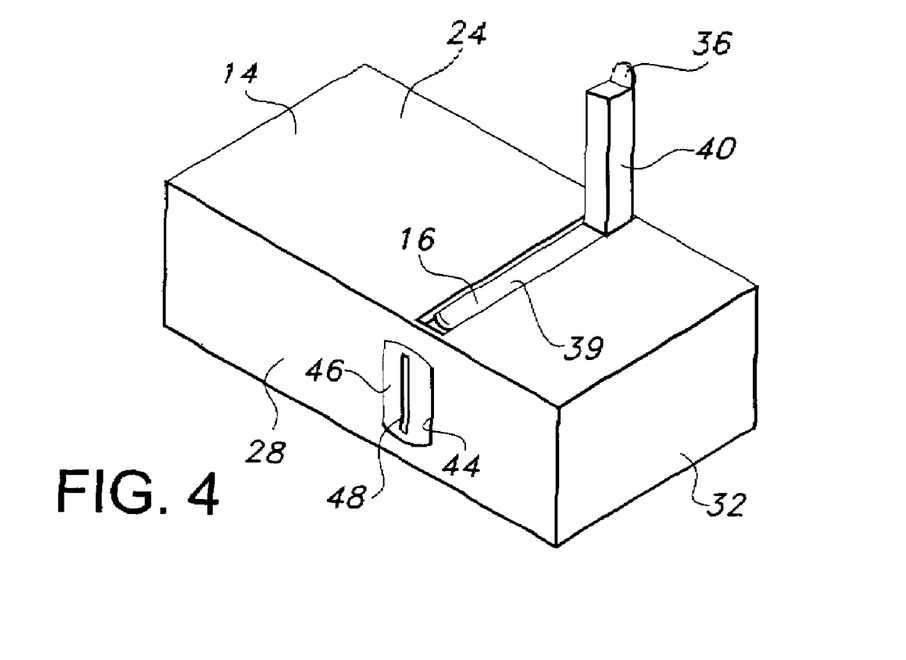
FIG. 4 is an upper perspective view of the cartridge of FIGS. 2 and 3, but showing the perforations separated to permit removal of the glove holder which is shown in a lifted and partially detached position, before the cartridge is inserted into the dispenser for dispensing, and illustrating a dispensing opening which is covered by an elastic membrane having a slit therein to permit a glove to be dispensed therethrough.

Referring now to FIGS. 1-10 in general, the present invention provides a dispensing assembly 10 including a dispenser 12 and a cartridge 14 which desirably holds a plurality of gloves 16, as shown in FIGS. 1 and 2. Each glove 16 desirably, but not by way of limitation, includes a wrist area 17 which is positioned around a user's wrist, which may, by way of example, be turned back over an adjacent portion of the glove 16 to provide a cuff (not shown). The gloves also include a palm area 19 and a finger/thumb area 20 as well. The plurality of gloves 16 are desirably aligned and positioned in a stack 22 of gloves 16 so that the wrist area 17 and cuff (if present) of one glove 16 is positioned next to and against the wrist area 17 of the glove 16 positioned directly above and/or below and against it in the cartridge 14. It will be understood that the gloves 16 may be provided in alternative alignment(s).

The cartridge 14 in the present embodiment desirably includes an upper wall 24 and a lower wall 26. The cartridge 14 also desirably includes a front wall 28, a back wall 30, and a pair of spaced-apart side walls 32, as shown in FIGS. 1-4. The front wall 28, back wall 30, and side walls 32 each cooperate with the upper wall 24 and lower wall 26 to provide an inner surface 34 which defines an internal compartment 35 configured to hold the plurality of gloves 16. It will be appreciated that the configuration of the cartridge 14 is non-limiting, and the cartridge 14 may assume any configuration or combination of configurations.

The cartridge 14 desirably includes a perforated area 36 which is defined by a plurality of perforations 38. The perforations 38 are desirably positioned across the upper wall 24 and extend from the front wall 28 to the back wall 30 of the dispenser 12 to create a removable strip when the perforations 38 are separated. The perforations 38 may extend into the front and/or back walls 28, 30 as well. An opening or slot may be provided by other means, such as a wall which is folded closed by which may be folded open, a partially or completely detachable wall, a seal which may be partially or completely removed that is used as a partial or complete wall, and so forth. The mechanism of providing an opening into the cartridge is not intended as a limitation. Turning back now to the present embodiment, attached to the perforated area 36 and positioned adjacent the plurality of gloves 16 is a glove holder 40. The glove holder 40 acts to hold the stack 22 of gloves 16 in a dispensing position in the cartridge 14 during shipment and storage. The glove holder 40 desirably contacts and extends across at least a portion of the wrist area 17 of the top glove 42 of the plurality of gloves 16 to hold the gloves in a stacked alignment for dispensing. The glove holder 40 may, but not by way of limitation, be formed from cardboard, paperboard, open or closed-cell foam rubber, or any material or combinations of materials which permit it to operate as shown and/or described herein. Alternatively, the cartridge may be provided without a glove holder (not shown).

The cartridge 14 also includes a dispensing opening 44 which may be covered by an elastic membrane 46 having a slit 48 therein. Alternatively, another perforated area may be provided via perforations, lines or areas of weakness, and so forth, and when the perforations are separated the perforated area removed, providing the dispensing opening (not shown). In yet another alternative, the perforated area 36 extends into the front wall 28 and when it is removed, provides the dispensing opening (not shown). The dispensing opening 44 may be provided in any wall or combination of walls, and it may be any size or configuration.

The cartridge 14 may also include a curved or raised portion 50, as shown in FIGS. 3, 6, 8 and 10, positioned on the lower wall 26 of the inner surface 34 of the cartridge 14, to facilitate dispensing of gloves 16 one at a time. The raised portion 50 is desirably aligned with the dispensing opening 44 and extends transversely between the front wall 28 and the back wall 30 of the cartridge. The raised portion 50 desirably extends underneath at least a portion of the wrist area 17 of the plurality of gloves 16. The raised portion 50 may be formed integrally with the cartridge 14, or it may be formed separately and coupled thereto. The raised portion 50 may be formed from any material or combination of materials. Alternatively, a dispenser housing 52 may include a raised portion (not shown) positioned across a lower wall 54 thereof or any wall and positioned generally in alignment with an exit port 55 and a dispensing opening 44 of the cartridge 14. The cartridge 14 may include perforations which are aligned at least generally with the raised portion of the dispenser housing 52 and separate when the cartridge 14 is positioned in the dispenser housing (not shown). In a further, similar alternative, such additional perforated area(s) is/are provided in the cartridge 14 and removed before the cartridge 14 is positioned in a dispenser housing 52 having a raised portion (not shown). It will be appreciated that the raised portion in either the cartridge 14 or the dispenser housing 52 may be positioned in any location therein and may assume any configuration(s). In yet another alternative, neither the cartridge 14 nor the dispenser housing 52 includes a raised portion (not shown).

The plurality of gloves 16 are desirably, but not by way of limitation, positioned wrist area 17 to wrist area 17, as illustrated in FIGS. 1 and 2. While the plurality of gloves 16 are shown positioned in a flat alignment, it may be desirable, once a stack 22 is created, to fold over and overlap at least a portion of the finger/thumb area 20 of the stack 22 upon itself, to conserve space in the cartridge 14 (not shown). Such a configuration of the stack 22 of gloves 16 may be desirable so that the cartridge 14 and its associated dispenser 12 are not too large in size and/or configuration.

Turning now to the dispenser 12, as shown in FIGS. 1 and 5-10, the dispenser 12 desirably may include the housing 52 having an outer surface 53 and the lower wall 54 and an upper wall 56. The housing 52 also desirably includes a front wall 58, a back wall 60 and a pair of spaced-apart sides walls 62, all of which cooperative to provide the housing 52, as well as an inner surface 64 and a cartridge compartment 65 in the housing 52. The cartridge compartment 65 is configured to receive and hold a cartridge 14 therein. The exit port 55 is desirably, but not by way of limitation, positioned through a portion of the front wall 58 in the present embodiment, and is desirably positioned to be in an alignment with the dispensing opening 44 of a cartridge 14, when it is positioned in the housing 52. As such, the exit port 55 may be positioned in any wall or combination of walls and it may be any size or configuration which permits it to operate as shown and/or described herein.

The exit port 55 may provide only an opening to permit passage of a glove 16 therethrough. The exit port 55 may, however, provide an elastic membrane 66 having a slit 67 therein to limit the ability of liquid, solid and/or air borne contaminants from entering the dispenser housing 52. Such an elastic membrane 66 for the housing 55 or the cartridge 14 are desirably formed from plastic, polymer, or any material(s) which operate as shown and/or described herein.

The upper wall 54 may be coupled to the back wall 60 via a pair of hinges 68, as shown in FIG. 1, or other fasteners (not shown) so that the upper wall 54 provides a lid 69 which is pivotably movable away from the remainder of the housing 55. In this manner, the lid 69 permits access to the cartridge compartment 65 and also provides closure to the housing 55 and cartridge compartment 65. The lid 69 desirably includes an opening such as a narrow slot 70 which is positioned transversely across a substantial portion of the lid 69. The slot 70 desirably is formed in the lid 69 in an alignment with the exit port 55. A glove pusher 72 may be coupled to an outer surface 53 such as an upper surface 74 of the lid 69 and/or an inner surface 39 such as a lower surface 76 of the lid 69, as illustrated in FIGS. 1 and 5-10.

The glove pusher 72 may include an upper plate 74 which is positioned across the slot 70, and which holds an actuator button 76. The glove pusher 72 may also include a lower plate 78 which may include a leg housing 80. The upper and lower plates 74, 78 may be coupled together or interconnected through the slot 70. The leg housing 80 desirably holds a glove moving means or glove contactor such as a movable leg 82 and foot 84 of the glove pusher 72, which is movable within the leg housing 80. The actuator button 76 is coupled via a shaft (not shown) positioned through the slot 70 and leg housing 80 to the movable leg 82 and moves the leg 82 and its foot 84 in a direction 86 generally, but not by way of limitation, upward and downward. The glove pusher 72 is desirably formed to move at least a portion of a glove out of the cartridge 14 and/or dispenser 12 and through the dispensing opening 44 and/or exit port 55. In the present embodiment, but not by way of limitation, the glove pusher 72 may be configured to be slidably movable across the length of the slot 70. Therefore, the actuator button 76 permits a user to slidably move the glove pusher 72 and therefore the leg 82 and foot 84 generally across the length 88 of the cartridge compartment 65 as well as in a direction 86 up and down within the cartridge compartment 65.

The actuator button 76 desirably includes an interlock (not shown) which locks the leg 82 and foot 84 at its highest, most upward elevation when the lid 69 is opened and closed, but releases when the button 76 is pushed or actuated to permit the leg 82 and foot 84 to drop against and firmly contact the top glove 42 in the stack 22 of gloves 16. The foot 84 may include frictional contacts (not shown) such as, by way of non-limiting example, ribs, rounded points, and so forth on the toe 92 and/or bottom 94 of the foot 84 so that the foot 84 is frictionally positioned against the top glove 42. The glove pusher 72 also desirably includes a tensioner 90 to permit the glove pusher to move across the length 88 of the cartridge compartment 88 and the slot 70 but tensions or biases the glove pusher 72 to return to its resting position (FIG. 5) adjacent the back wall 60 of the dispenser housing 52, and the back wall 30 of the cartridge 14. Such a tensioner 90 may include, by way of non-limiting example, a spring, an elastic or rubber ring (not shown), and so forth.

The cartridge 14 and the dispenser 12 may be made from any material or combinations of materials and may have any configuration(s) which permit the cartridge and the dispenser to operate as shown and/or described herein. That is, the cartridge may be constructed from, by way of non-limiting example, cardboard, paper board, plastic, polymer film, and so forth. The dispenser 12, or any portion(s) thereof may, but not by way of limitation, be formed from such material as metal, plastic, cardboard, paperboard, polymer film, and so forth.

In a method of use, illustrated in FIGS. 1 and 4-10. a dispenser 12 and a cartridge 14 having a plurality of gloves 16 therein is provided. The perforated area 36 is separated and removed from the cartridge 14. The lid 69 of the housing 52 is lifted and the cartridge 14 is inserted therein such that the opening 39 formed by removal of the perforated area 36 is aligned with the opening or slot 70 in the wall or lid 69 of the housing 52, and the dispenser opening 44 of the cartridge 14 is aligned with the exit port 55 of the housing 12. The lid 69 is closed and the leg housing 80 with the leg 82 and foot 84 extending therefrom is inserted into the opening 39 of the cartridge 14.

Figure 5:
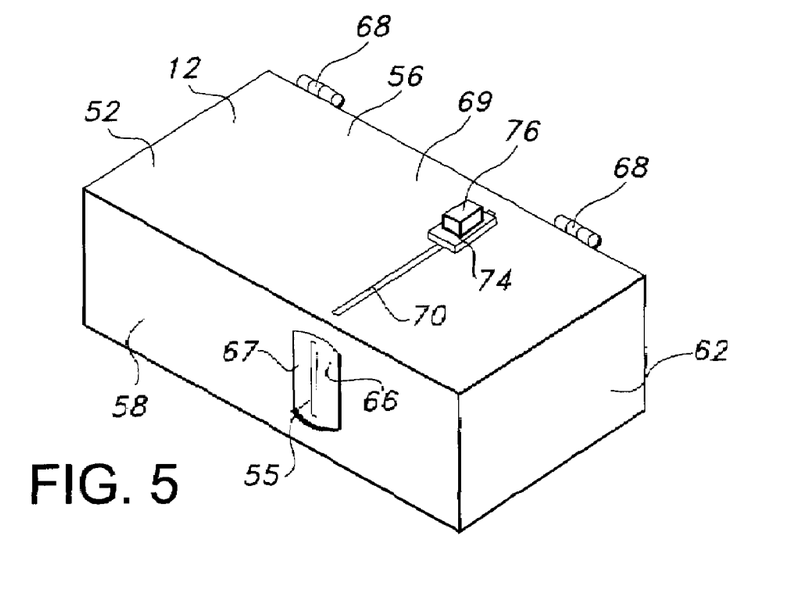
FIG. 5 is an upper perspective view of the dispensing assembly of FIG. 1, showing the lid of the dispenser closed and a cartridge positioned therein, a button of the glove pusher positioned on the lid and configured to slide in a slot formed across the lid.
Figure 6:
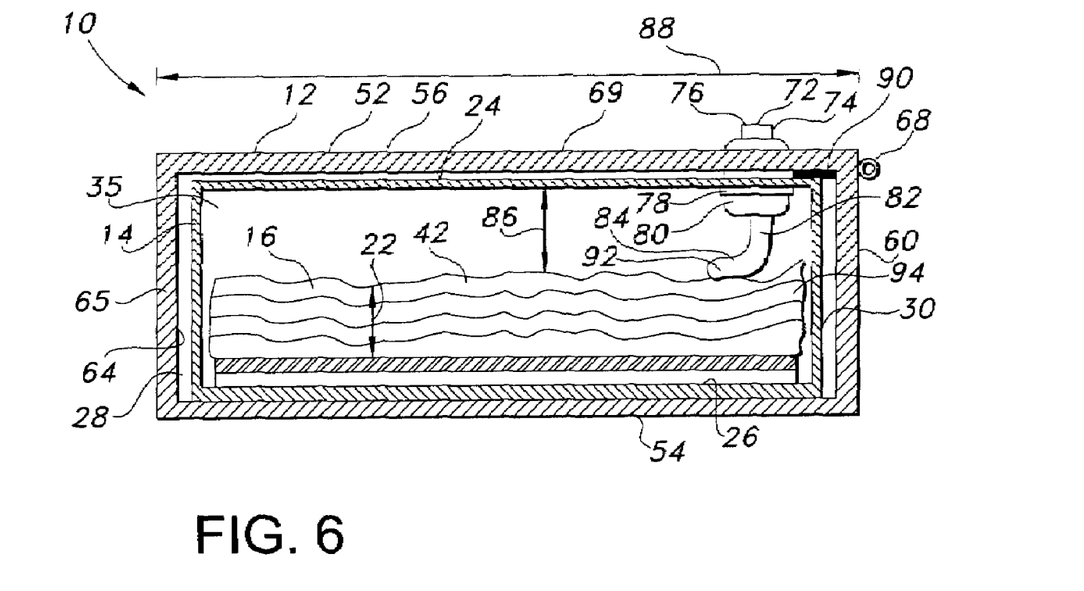
FIG. 6 is a sectional view of FIG. 5 taken along lines 6-6, showing a glove pusher disposed on a top glove in a stack of gloves in the cartridge, the glove pusher positioned to push the top glove when the button is moved across the slot in the lid, the glove pusher having a leg and a foot which pushes the top glove.
Figure 7:
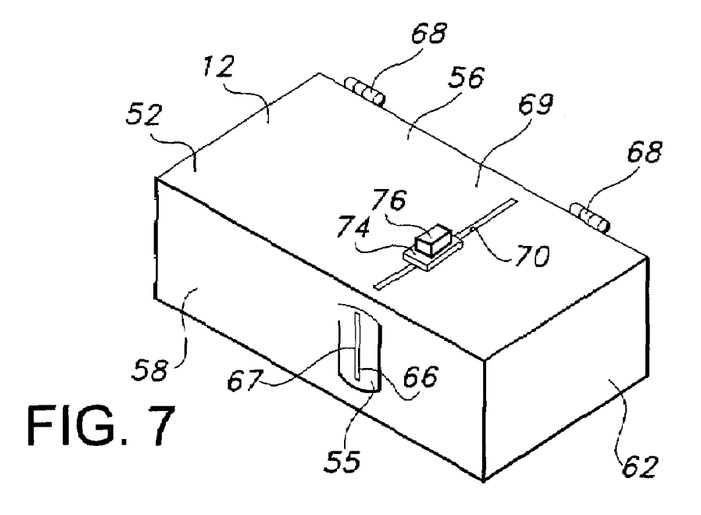
FIG. 7 is an upper perspective view of the dispensing assembly similar to the dispensing assembly shown in FIG. 5, but showing the button of the glove pusher in a positioned about half of the way across the slot in the lid.
Figure 8:
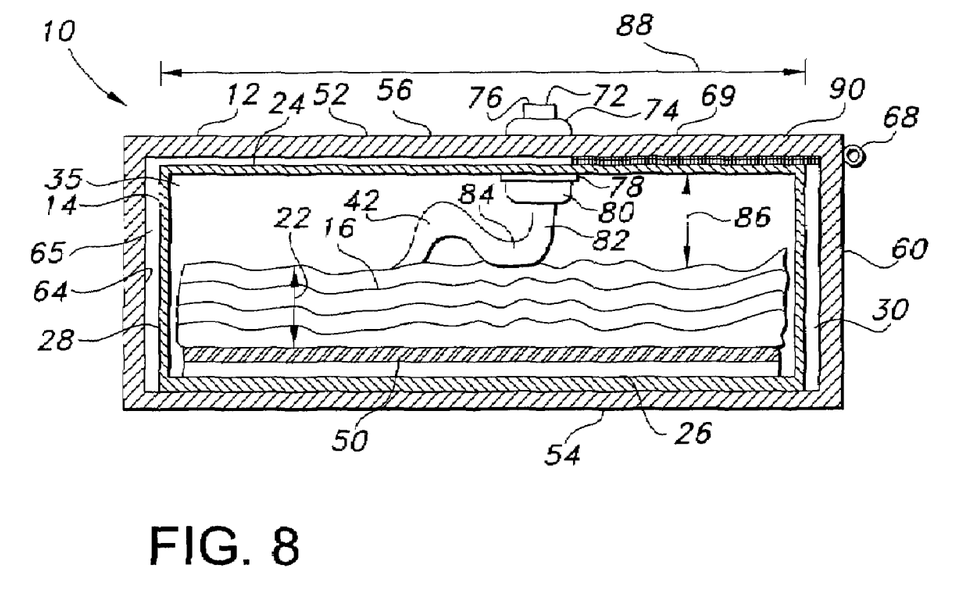
FIG. 8 is a sectional view taken along lines 7-7, showing the glove pusher with its leg and foot in a pushing position, pushing the top glove as the button is moved by a user across the slot, thereby causing the top glove to bunch or ruffle around the foot and leg.
Figure 9:
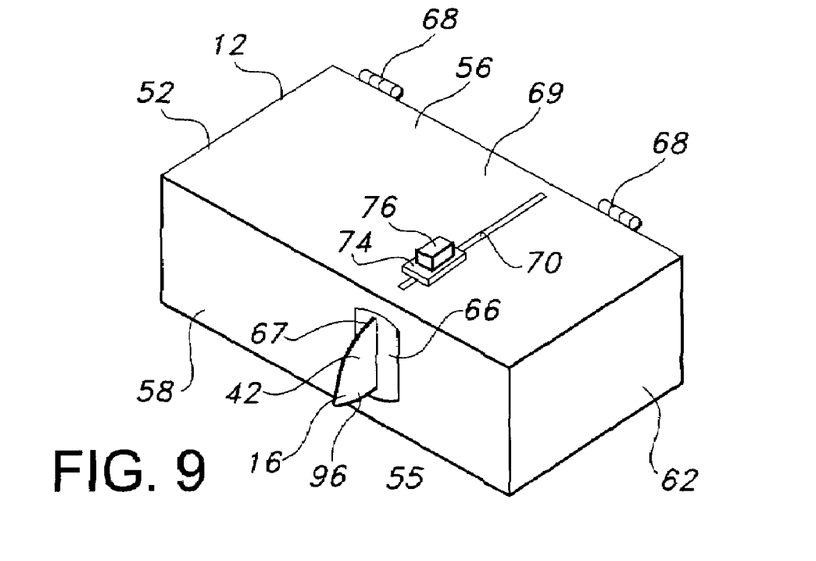
FIG. 9 is an upper perspective view of the dispensing assembly similar to the dispensing assembly shown in FIG. 7, but showing the button of the glove pusher position across the lid near an exit port in the dispenser, a portion of the top glove positioned through the exit port such that a user may grasp the single glove and withdraw it from the cartridge and dispenser for use.
Figure 10:
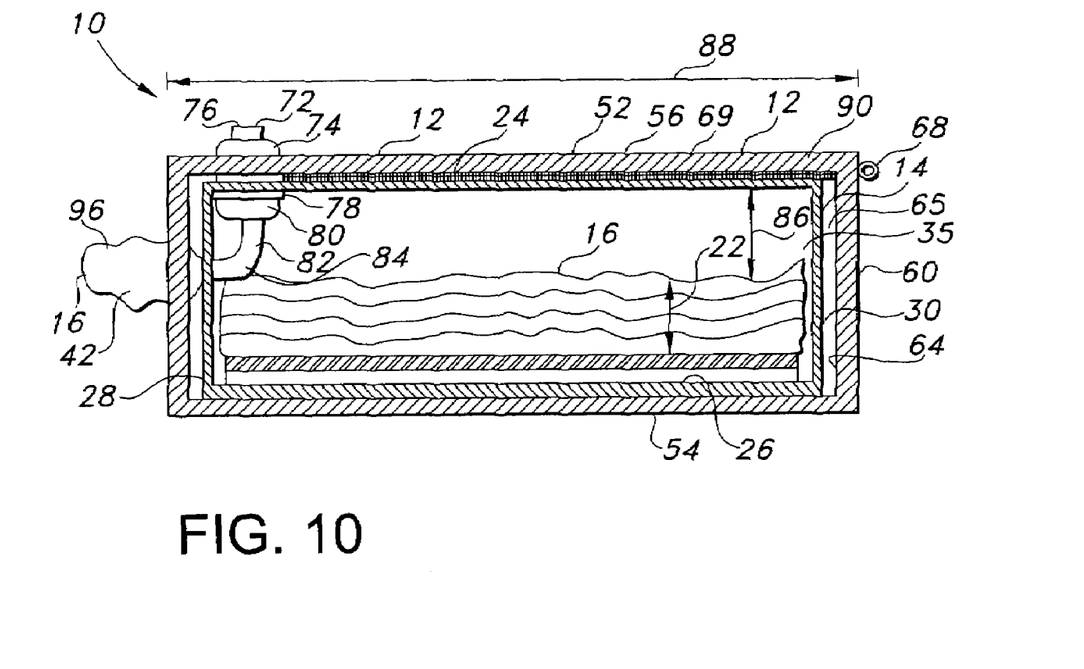
FIG. 10 is a sectional view taken along lines 10-10, showing the glove pusher fully extended across the cartridge and the dispenser and the foot pushing a portion of the top glove through both the dispensing opening of the cartridge and the exit port of the dispenser.

The glove pusher 72 is positioned in its resting position with its leg 82 positioned adjacent the back wall 60 of the housing 52 and the back wall 30 of the cartridge 14. When a user desires to obtain a glove 16, the user pushes the actuator button 76, which releases the interlock and drops the leg 82 and foot 84 downward in the direction 86 such that the foot 84 firmly contacts the top glove 42 in the stack 22 of gloves 16, as shown in FIG. 6. The user then pushes the button 76 across the slot 70 in the lid 69 toward the front wall 58 of the housing 52. This action causes the foot 84 of the glove pusher 72 to push against the top glove 42 and begin bunching or ruffling upward the top glove 42 such that it bunches upward around the toe 92 and foot 84 of the glove pusher 72, as shown in FIGS. 7 and 8. When the glove pusher 72 is moved to its maximum extended position adjacent the front walls 28, 58 of the cartridge 14 and the housing 52, the toe 92 and foot 84 of the glove pusher 72 push the bunched and ruffled portion of the top glove 42 positioned about and around the toe 92 and foot 84 through the slit 42 in the elastic membrane 46 of the dispensing opening 44 of the cartridge and through the slit 67 and the elastic membrane 66 of the exit port 55 of the dispenser housing 52 such that a portion 96 of the top glove 42 extends away from the dispenser housing 52 for a user to grasp and withdraw the remainder of the top glove 42 therefrom. When the actuator button 76 is released by a user, the tensioner 90 moves the glove pusher 72 back across the slot 70 in the lid 72 to its resting position adjacent the back wall 30 of the cartridge 14 and/or the back wall 60 of the housing 52, as illustrated in FIGS. 5 and 6. It will be appreciated that the glove 16 below the top glove 42 becomes the new top glove when the previous top glove is removed. The method is repeated until each of the plurality of gloves 16 in the stack 22 are removed from the cartridge 14 by the glove pusher 72. In this manner, the dispensing assembly provides one-at-a-time dispensing of gloves from a cartridge positioned in the dispenser.

It will be understood that the dispenser 12 may receive a plurality of gloves 16 directly within the dispenser housing 52. The glove pusher may then be actuated as previously described herein to dispense gloves one at a time.

It will also be understood that a lever or other mechanical actuator may be used in place of the described button. Further, it will be understood that the dispenser may be oriented or aligned as shown, upside down, on any or its side(s), or in an oblique alignment. All openings may be formed in any wall or combination of walls so long as the dispenser and/or cartridge operate to dispense at least one glove. Moreover, the dispenser may be battery operated or electrically connected to a power source in order to dispenser at least one glove.

While the present invention has been described in connection with certain preferred embodiments, it is to be understood that the subject matter encompassed by way of the present invention is not to be limited to those specific embodiments. On the contrary, it will be appreciated that some elements and/or articles may be used with other elements or articles. It is intended for the subject matter of the invention to include all alternatives, modifications and equivalents as can be included within the spirit and scope of the invention.

What is claimed is:

1. A dispenser for dispensing gloves, the dispenser comprising:
   a housing formed to include a compartment therein, the housing configured to hold a plurality of gloves in the compartment, the housing including a raised portion and an exit port, the raised portion extending underneath a wrist area of each one of the plurality of gloves; and
   a glove pusher movably coupled to the housing, at least a portion of the glove pusher configured to move within the compartment of the housing and push at least a portion of a glove disposed in the compartment through the exit port;
   the glove pusher comprising an actuator button, and a leg and a foot coupled to the actuator button; the actuator button, the leg, and the foot being linearly movable in a direction generally parallel to the gloves; and
   the actuator button further comprising an interlock which locks the leg and foot at its highest elevation, and releases the leg and foot when the actuator button is linearly moved to permit the leg and foot to firmly contact a glove in the compartment.

2. The dispenser of claim 1, wherein the housing includes a lid, the lid including an opening and at least a portion of the glove pusher extends through the opening and into the compartment of the housing.

3. The dispenser of claim 2, wherein the opening is aligned with the exit port.

4. The dispenser of claim 1, wherein the actuator button moves the leg and foot vertically.

5. The dispenser of claim 1, wherein the glove pusher is configured to move the leg and foot horizontally.

6. The dispenser of claim 1, wherein the foot includes frictional contacts so that the foot frictionally contacts a portion of a glove in the compartment.

7. The dispenser of claim 1, wherein the glove pusher includes tensioner which tensions the glove pusher to return and remain adjacent a wall of the housing when in a resting position.

8. The dispenser of claim 1, wherein the glove pusher is configured to be positioned against and contact a glove in the compartment and to move at least a portion of a glove across the compartment when the actuator button is moved across the opening toward the exit port such that at least a portion of a glove is pushed through the exit port when the glove pusher is moved across the perimeter length of the opening and positioned adjacent the exit port.

9. The dispenser of claim 1 further comprising a replaceable cartridge adapted to hold the plurality of gloves, the cartridge configured to be positioned in the compartment and to permit at least one of the plurality of gloves to be moved at least partially through the at least one opening in the cartridge.

10. The dispenser of claim 9, wherein the cartridge includes a removable strip which provides the opening into the cartridge.

11. The dispenser of claim 10, wherein a glove holder is carried by the removable strip.

12. The dispenser of claim 11, wherein the glove holder holds the plurality of gloves in a position in the cartridge and limits movement of the gloves in the cartridge.

13. The dispenser of claim 10, wherein the opening in the cartridge permits the glove pusher to be positioned in the cartridge such that a glove is positioned to contact the glove pusher.

14. The dispenser of claim 9, wherein the at least one opening in the cartridge includes a dispensing opening.

15. The dispenser of claim 14, wherein the dispensing opening is positioned in the cartridge to be aligned with the exit port in the dispenser when the cartridge is disposed in the dispenser.

* * * * *